(12) United States Patent
Sen et al.

(10) Patent No.: US 6,232,257 B1
(45) Date of Patent: May 15, 2001

(54) PREPARATION OF HIGHLY BRANCHED, LIQUID POLYMERS OF ETHYLENE AND/OR α-OLEFINS IN THE PRESENCE OF ALUMINUM-BASED CATALYST SYSTEMS

(75) Inventors: Ayusman Sen; Louis M. Wojcinski, II; Shahid Murtuza, all of State College, PA (US)

(73) Assignee: The Penn State-Research Foundation, University Park, PA (US)

( * ) Notice: Subject to any disclaimer, the term of this patent is extended or adjusted under 35 U.S.C. 154(b) by 0 days.

(21) Appl. No.: 09/273,127

(22) Filed: Mar. 19, 1999

Related U.S. Application Data

(60) Provisional application No. 60/078,695, filed on Mar. 20, 1998.

(51) Int. Cl.$^7$ ..................................................... B01J 31/02
(52) U.S. Cl. ........................ 502/114; 585/520; 585/522; 585/523
(58) Field of Search ............................. 585/520, 522, 585/523; 502/114

(56) References Cited

U.S. PATENT DOCUMENTS

| | | | | |
|---|---|---|---|---|
| 3,725,497 | * | 4/1973 | Arakawa et al. | 260/683.15 D |
| 3,852,373 | * | 12/1974 | Hesse et al. | 260/680 B |
| 4,533,782 | * | 8/1985 | Merijanian | 585/522 |
| 4,735,931 | | 4/1988 | McDaniel et al. | 502/107 |
| 5,616,529 | | 4/1997 | Ostoja-Starzewski et al. | 502/154 |
| 5,686,542 | | 11/1997 | Ostoja-Starzewski et al. | 526/75 |
| 5,777,120 | | 7/1998 | Jordan et al. | 546/2 |
| 6,069,213 | * | 5/2000 | Nemzek | 526/113 |

FOREIGN PATENT DOCUMENTS

| | | |
|---|---|---|
| 0250 999 B1 | 1/1992 | (EP) . |
| 0727 446 A1 | 8/1996 | (EP) . |
| WO 94/07930 | 4/1994 | (WO) . |
| WO 96/07680 | 3/1996 | (WO) . |
| WO 96/23010 | 8/1996 | (WO) . |
| WO 97/48735 | 12/1997 | (WO) . |
| WO 98/33823 | 8/1998 | (WO) . |
| WO 98/40421 | 9/1998 | (WO) . |

OTHER PUBLICATIONS

Martin, et al., *Makromol. Chem.,* vol. 193, pp. 1283–1288 (1992) (no month).
Coles, et al., *J. Am. Chem. Soc.,* vol. 119, pp. 8125–8126 (1997) (no month).
de Souza, et al; *Makromol. Rapid Commun.,* vol. 18, pp. 795–801 (1997) no month.
Pappalardo, et al, *Makromol. Rapid Commun., ,* vol. 18, pp. 1017–1023 (1997) no month.
Beach et al, *J. Polym. Sci: Polym. Chem. Ed.,* vol. 22, pp. 3027–3042 (1984) (no month).
Barnhart, et al, *J. Am. Chem. Soc.,* vol. 120, pp. 1082–1083 (1998) no month.
Kim, et al, *J. Am. Chem. Soc.,* vol. 120, pp. 1932–1933 (1998) no month.

* cited by examiner

*Primary Examiner*—David W. Wu
*Assistant Examiner*—Ling-Siu Chol

(57) ABSTRACT

Ethylene and/or propylene are polymerized to form highly branched, liquid polymers by contacting ethylene and/or propylene monomer, in the presence of an inert reaction medium, with a catalyst system which comprises (1) an alkyl aluminum component, (2) an aluminum or gallium trihalide component, and, optionally, (3) a Group 4 metallocene dihalide component.

4 Claims, No Drawings

PREPARATION OF HIGHLY BRANCHED, LIQUID POLYMERS OF ETHYLENE AND/OR α-OLEFINS IN THE PRESENCE OF ALUMINUM-BASED CATALYST SYSTEMS

RELATED APPLICATIONS

This application is based on Provisional Application No.60/078,695, filed Mar. 20, 1998, the disclosure of which is incorporated herein by reference.

BACKGROUND OF THE INVENTION

1. Field of the Invention

This invention relates to highly branched, liquid polymers of ethylene and/or α-olefins, e.g., propylene, which are prepared in the presence of an aluminum-based catalyst system, optionally containing a transition metal component. The polymers prepared in accordance with this invention have unique properties and are useful, for example, as thickeners and as lubricants and/or lubricant additives. An advantage of the present invention is that it enables the synthesis of highly branched ethylene and α-olefin polymers without the need for transition metal catalyst components, thereby avoiding disposal problems typically associated with the use of transition metal-based catalysts.

2. State of the Art

Polymerization of ethylene in the presence of transition metal-based catalysts usually results in the formation of solid, linear polymers. As such, they are not suitable as soft materials or lubricants for most applications.

For a hydrocarbon polymer having a molecular weight more than about 350 to remain liquid, the polymer typically must contain significant branching. An example of such moderately branched hydrocarbon polymers can be found in PCT Int. Appl. WO96/23010 (1996). In that PCT application, it is disclosed that polymers having a moderate degree of branching can be synthesized by using palladium and nickel catalysts incorporating very bulky chelating α-diimine bidentate ligands. The PCT application discloses, for example, polyolefins having about 80 to about 150 branches per 1000 methylene groups, wherein for every 100 branches that are methyl branches, there are about 30 to about 90 ethyl branches, about 4 to about 20 propyl branches, about 15 to about 50 butyl branches, about 3 to about 15 amyl branches, and about 30 to about 140 hexyl or longer branches. The olefin polymers described in the PCT application are said to be useful as elastomers, molding resins, and in adhesives. Polymers containing monomer units derived other than from olefins are also disclosed in the PCT application; and polymers which contain olefin and olefinic ester monomer units, particularly copolymers of ethylene and methyl methacrylate and/or other acrylic esters, are said to be useful as viscosity modifiers for lubricating oils.

Oily hyperbranched polymers derived from ethylene, propylene, butene and/or other α-olefins, and a method for their synthesis, are disclosed in WO98/33823 (1998), which is assigned to the assignee of the present application. WO98/33823 discloses polymers having non-regular microstructures characterized by a ratio (R) of methyl hydrogens centered around 0.85 ppm on the 1H-NMR spectra of the polymers relative to total aliphatic hydrogens of from about 0.40 to about 0.65 for polymers derived from ethylene or butene, and a ratio (R) of from greater than 0.50 to about 0.65 for polymers derived from propylene. However, the catalyst system employed to synthesize the hyperbranched polymers described in WO98/33823 is transition metal-based and differs significantly from the aluminum-based catalyst system contemplated in the present invention.

Other disclosures that describe nickel-based catalyst systems for ethylene polymerization include, for example, *Macromol. Rapid Commun.* 1997, 18, 795, which discloses using a catalyst system comprising nickel α-diimine compounds, and *Macromol. Rapid Commun.* 1997, 18, 1017, which discloses using a catalyst system comprising a [η3-methylallyl-nickel-dad]$PF_6$ complex that is active in the presence of an organoaluminum compound. The polymers that are formed using the catalysts systems that are described in the above references are significantly less branched that the polymers prepared in accordance with the present invention.

Other catalyst systems that are useful for the synthesis of moderately branched polymers from ethylene have been disclosed. See, for example, *J. Polym. Sci. Chem. Ed.* 1984, 22, 3027; U.S. Pat. No. 4,735,931 (1988); PCT Int. Appl. WO94/07930 (1994); EP 0 727 446 A1 (1996); PCT Int. Appl. WO96/07680 (1996); PCT Int. Appl. WO97/48735 (1997); EP 0 250 999 B1 (1997); U.S. Pat. No. 5,686,542 (1997); and *J. Am. Chem. Soc.* 1998, 120, 1082. The catalyst systems that are described in the above references typically are based on transition metal Ziegler-type or metallocene catalysts and result in polymers that are essentially linear or only moderately branched.

More highly branched polymers of ethylene (having a degree of branching comparable with that of the polymers prepared in accordance with the present invention) are described in *J Am. Chem. Soc.* 1998, 120, 1932. The polymers that are disclosed in that reference are prepared in the presence of a Group 10 transition metal-based catalyst, e.g., a Ni- or Pd-based catalyst. Accordingly, the process disclosed in that reference is typical in the sense that it must deal with the disposal of transition metal components.

There have been few reports of transition metal free catalyst systems that are useful for the synthesis of polymers from ethylene and/or α-olefins. One such report (*Makromol. Chem.*, 1992, 193, 1283) discloses an aluminum based catalyst system that produces polymers that are "largely linear" and are characterized by molecular weights of at least 300,000. In a more recent report (*J. Am. Chem. Soc.*, 1997, 119, 8125), an aluminum catalyst containing nitrogen-based ligands was disclosed for the synthesis for hydrocarbon polymers. However, the polymers that were disclosed in that report were not significantly branched. Similarly, U.S. Pat. No. 5,777,120 discloses cationic aluminum amidinate compounds that are useful Ziegler Natta-like olefin polymerization catalysts, and WO98/40421 discloses cationic complexes comprising a Group 13 element and certain ligands that behave like Ziegler-Natta polymerization catalysts in the absence of any transition metal. The polymers that are prepared using the catalysts of both U.S. Pat. No. 5,777,120 and WO98/40421 are essentially linear polymers of ethylene.

While great strides have been made in the search for new and improved ethylene and α-olefin polymerization catalysts, there remains a need for catalyst systems that are not based primarily on transition metals, that require only commercially available aluminum-based components, that require no ligand substitution, and that, nonetheless, are capable of efficiently converting ethylene and/or olefin monomer(s) to highly branched, liquid polymers under otherwise conventional polymerization reaction conditions.

SUMMARY OF THE INVENTION

Until the present invention, it has generally not been possible to synthesize relatively high molecular weight, significantly branched hydrocarbon polymers (i.e., liquid polymers) from simple inexpensive olefins such as ethylene and propylene, using simple and relatively inexpensive aluminum-based catalyst components.

In accordance with the present invention, such highly branched, liquid polymers from olefins, such as ethylene and propylene, are synthesized by contacting the selected monomer(s), in the presence of a suitable reaction medium and under otherwise conventional polymerization reaction conditions, with a catalyst system that comprises an alkyl aluminum compound and an aluminum or gallium trihalide as the only essential components. Optionally, a Group 4 metal component may be added to the catalyst system; but in preferred aspects of the invention, the catalyst system is free from any transition metal components so as to avoid any disposal problems that typically are associated with the use of transition metal-based catalysts.

Typical alkyl aluminum compounds that are suitable for use in this invention are the aluminoxanes, such as methylaluminoxane (hereinafter referred to as "MAO") or alkyl aluminum compounds having the formula $R_xAlX_{3-x}$, where R is a hydrocarbyl group, X is a halide (e.g., Cl or Br), and $0 < x \leq 3$.

Alkyl aluminum compounds that are suitable for use in this invention include, for example, ethylaluminum dichloride, diethylaluminum chloride, triethyldialuminum trichloride, triethylaluminum, diethylaluminum bromide, methylaluminum dichloride or the like.

Typical aluminum or gallium trihalide compounds that are suitable for use in this invention are aluminum trichloride, aluminum tribromide, gallium trichloride or the like.

Although it is preferred to use a catalyst system that is free from any transition metal components so as to avoid disposal problems, the optional use of a Group 4 transition metal component in combination with the alkyl aluminum component and the aluminum trihalide component is within the scope of this invention. When present as part of the catalyst system, the optional Group 4 metal component typically is a Group 4 metallocene dihalide, such as bis(cyclopentadienyl)zirconium dichloride. Other Group 4 metal components that may be used as an optional componet include, for example, bis(cyclopentadienyl)titanium dichloride, bis(cyclopentadienyl)hafnium dichloride, or the like.

The polymerization typically is carried out by contacting the selected monomer (e.g., ethylene and/or propylene) in an inert polar solvent (e.g., chlorobenzene), although hydrocarbon solvents (e.g., hexane) can be used. The polymerization reaction is carried out at a temperature of about −20 to 150° C., typically from about 25 to about 100° C., e.g. 50° C., and a pressure of from about 15 to about 1,500 psi, typically from about 200 to about 1,000 psi, e.g., 800 psi. The polymerization reaction typically would be allowed to proceed for a period of from about 1 hour to about 48 hours, and more typically from about 4 to about 24 hours, after which the polymerization reaction would be terminated by conventional means, e.g., by adding methanol or another conventional polymerization stopper to the reaction mass.

The catalyst system of this invention is indeed capable of polymerizing ethylene and α-olefins, particularly propylene, under conventional reaction conditions, to form liquid polymers having a very high degree of branching. The degree of branching can be estimated from the ratio of methyl hydrogens centered around 0.85 ppm in the $^1$H NMR spectrum ($H_{Me}$) to the total alkyl hydrogens ($H_{Tot}$) for a given polymer, with a higher ratio ($H_{Me}/H_{Tot}$) indicating a higher degree of branching. For linear polyethylene the ratio ($H_{Me}/H_{Tot}$) is 0. For polymers obtained from ethylene in accordance with the present invention, $0.40 < H_{Me}/H_{Tot} < 0.60$.

DESCRIPTION OF PREFERRED EMBODIMENTS

The preparation of highly branched, liquid polymers of ethylene and α-olefins, e.g., propylene, is achieved in accordance with one preferred aspect of the invention by contacting ethylene and/or propylene, in the presence of an inert solvent, and under polymerization reaction conditions, with a catalyst which comprises (1) an alkyl aluminum component and (2) an aluminum trihalide component as the only essential components. Optionally, the catalyst may also comprise a Group 4 metal compoonent, typically a Group 4 metallocene dihalide.

The monomers that may be polymerized in accordance with this invention include ethylene and propylene, as well as other α-olefins, such as butene.

The monomers may be polymerized singly to form homopolymers, such as polyethylene or polypropylene. In the alternative, two or more monomers may be mixed and polymerized simultaneously to form copolymers, such as ethylene-propylene copolymers. Typically, the present invention would be used to prepare highly branched, liquid, polyethylene and polypropylene products having a number average molecular weight ($M_n$), determined relative to polystyrene standards, on the order of from about 5,000 to about 200, preferably from about 3,000 to about 300, and more preferably from about 1,500 to about 400.

The resulting polymer products would be characterized by having a very high degree of branching. The degree of branching can be estimated from the ratio of methyl hydrogens centered around 0.85 ppm in the $^1$H NMR spectrum ($H_{Me}$) to the total alkyl hydrogens ($H_{Tot}$) for a given polymer, with a higher ratio ($H_{Me}/H_{Tot}$) indicating a higher degree of branching. For linear polyethylene the ratio ($H_{Me}/H_{Tot}$) is 0. For polymers obtained from ethylene in accordance with the present invention, the ratio of $H_{Me}$ to $H_{Tot}$ would be between about 0.40 and 0.60, i.e., $0.40 < H_{Me}/H_{Tot} < 0.60$. Similarly branched polymers would be obtained from propylene and other α-olefins that are synthesized in the presence of the present catalyst system.

The polymerization preferably is carried out in the presence of an inert solvent, with polar solvents, such as chlorobenzene, being preferred over hydrocarbon solvents, such as hexane. Polar solvents which may be used in lieu of chlorobenzene, or in addition to chlorobenzene include, for example, dichlorobenzene, trichlorobenzene, tetrachloroethane and the like. Hydrocarbon solvents which may be used in lieu of hexane, or in addition to hexane include, for example, decane and benzene.

The polymerization typically is carried out by contacting the selected monomer and the catalyst system at a temperature of about −20 to 150° C., and more typically from about 25 to about 100° C., e.g. 50° C., and at a pressure of from about 15 to about 1,500 psi, typically from about 200 to about 1,000 psi, e.g., 800 psi. The polymerization may be performed in conventional apparatus and in a conventional manner, except that the present catalyst system would be used in place of the currently employed transition metal-based catalyst systems. The polymerization may be performed in a continuous process, a semi-continuous process, or a batch process, as desired. Typically, the polymerization would be allowed to proceed for a period of from about 1 hour to about 48 hours, and more typically from about 4 to about 24 hours, after which the polymerization reaction would be terminated by conventional means, e.g., by adding methanol or another conventional polymerization stopper to the reaction mass.

The catalyst system of this invention does not require the presence of a transition metal component. The only essential components of the catalyst system are (1) an alkyl aluminum component and (2) an aluminum or gallium trihalide component.

The alkyl aluminum components contemplated for use in this invention comprise aluminoxanes, such as methylaluminoxane (MAO), and alkyl aluminum compounds of the formula $R_xAlX_{3-x}$, where R is a hydrocarbyl group, X is a halide (e.g., Cl or Br), and $0<x\leq3$. Representative examples of alkyl aluminum compounds that are suitable for use in this invention include, for example, ethylaluminum dichloride, diethylaluminum chloride, triethyldialuminum trichloride, triethylaluminum, diethylaluminum bromide, methylaluminum dichloride or the like.

Typical aluminum or gallium trihalide compounds that are suitable for use in this invention are aluminum trichloride, aluminum tribromide and gallium trichloride. Although it is preferred to use a catalyst system that is free from any transition metal components to avoid disposal problems, the use of an optional Group 4 transition metal component is within the scope of this invention. When present as part of the catalyst system, the optional Group 4 metal component typically is a metallocene dihalide, such as bis(cyclopentadienyl)zirconium dichloride. Other Group 4 metal components that may be used as an optional component include, for example, bis(cyclopentadienyl)titanium dichloride, bis(cyclopentadienyl)hafnium dichloride, or the like. The invention will be appreciated more fully in light of the following example, which is intended merely to illustrate the invention, and not to limit the scope thereof.

EXAMPLE

Ethylene Polymerization via Aluminum Catalysis

In a series of polymerization runs, ethylene was polymerized at 50° C. in the presence of the catalyst system and reaction solvent indicated in Table 1. Each polymerization run was carried out in a stainless steel 125 ml pressure vessel equipped with a glass liner. For each run, the catalyst system, mixed in 10 ml of solvent, was introduced into the pressure vessel in a nitrogen-filled glove box. Then, after removing the assembled pressure vessel from the glove box, the vessel was charged with ethylene, and the reaction was allowed to continue for the indicated time. The reaction vessel was then vented, and the reaction mixture was poured, with stirring, into acidic methanol to kill the polymerization. The polymer was stirred overnight, separated, and vacuum dried overnight. For each run, the resulting polymer was analyzed for yield and degree of branching, i.e., $H_{Me}/H_{Tot}$. The data observed for each run is set forth in Table 1.

TABLE 1

Ethylene polymerization via aluminum catalysis

| Run | mmol | Catalyst | Equiv. $AlCl_3$ | Solvent | Pressure (psi) | Yield (g) | $M_n^a$ | $M_w^a$ | $H_{Me}H_{Tot}$ |
|---|---|---|---|---|---|---|---|---|---|
| 1[b] | 0.85 | MAO[c] | 1 | $C_6H_5Cl^d$ | 800 | 4.0 | 1100 | 1390 | 0.44 |
| 2 | 8.6 | MAO[c], | 1 | $C_6H_5Cl$ | 800 | 3.9 | 1000 | 1190 | 0.46 |
|   | 0.017 | $Cp_2ZrCl_2$ |   |   |   |   |   |   |   |
| 3 | 0.36 | $C_2H_5AlCl_2^e$ | 2.2 | $C_6H_5Cl$ | 50[f] | 4.1 | 1090 | 1930 | 0.45 |
| 4 | 0.21 | $C_2H_5AlCl_2^e$ | 4 | $C_6H_5Cl$ | 700[f] | 11.9 | 760 | 1030 | 0.43 |
| 5 | 0.20 | $C_2H_5AlCl_2^e$ | 4 | Hexane | 700[f] | 4.9 | 730 | 990 | 0.45 |
| 6 | 0.80 | $C_2H_5AlCl_2^e$ | 0.25 | $C_6H_5Cl$ | 700 | 2.0 | 700 | 930 | 0.43 |
| 7 | 0.20 | $(C_2H_5)_3Al$ | 4 | $C_6H_5Cl$ | 700 | 3.2 | 540 | 720 | 0.49 |
| 8 | 0.10 | $(C_2H_5)_3Al_2Cl_3$ | 2 | $C_6H_5Cl$ | 700 | 2.8 | 480 | 670 | 0.56 |
| 9 | 0.20 | $(C_2H_5)_2AlCl$ | 4 | $C_6H_5Cl$ | 700 | 0.8 | 560 | 750 | 0.49 |

Reaction conditions: 50° C., 10 ml solvent, and single charge of ethylene, 24 hr. reaction time, unless otherwise noted.
[a] = Determined by gel permeation chromatography in $CHCl_3$ solution, relative to polystyrene standards.
[b] = 4 hr. hr. reaction time.
[c] = methylaluminoxane, 10 wt. % Al in toluene.
[d] = 20 ml.
[e] = 1.0M solution in hexane.
[f] = Constant feed.

What is claimed is:

1. A catalyst system for synthesizing branched, liquid polymers of ethylene and α-olefins, consisting essentially of (1) an alkyl aluminum component and (2) an aluminum or gallium trihalide component.

2. The catalyst system according to claim 1, wherein said alkyl aluminum component comprises at least one member selected from the group consisting of aluminoxanes and alkyl aluminum compounds having the formula $R_xAlX_{3-x}$, where R is a hydrocarbyl group, X is a halide, and $0<x\leqq3$.

3. The catalyst system according to claim 2, wherein said aluminum or gallium trihalide comprises aluminum trichloride.

4. The catalyst system according to claim 3, further consisting essentially of a Group 4 metallocene dihalide.

* * * * *